United States Patent [19]

Buchanan, Jr.

[11] 4,088,359
[45] May 9, 1978

[54] CONTACT LENS INSERTER

[76] Inventor: Richard S. Buchanan, Jr., Elmira Medical Arts Center, Elmira, N.Y. 14901

[21] Appl. No.: 760,976

[22] Filed: Jan. 21, 1977

[51] Int. Cl.² .............................................. A61F 9/00
[52] U.S. Cl. .................................................. 294/1 CA
[58] Field of Search .................... 294/1 CA, 64 R, 25; 128/303

[56] References Cited

U.S. PATENT DOCUMENTS

| 3,031,918 | 5/1962 | Moyers | 294/1 CA |
| 3,132,887 | 5/1964 | Martinez | 294/1 CA |
| 3,490,806 | 1/1970 | Lopez-Calleja et al. | 294/1 CA |
| 3,645,576 | 2/1972 | Horres | 294/1 CA |

Primary Examiner—James B. Marbert
Attorney, Agent, or Firm—Victor J. Evans & Co.

[57] ABSTRACT

An instrument for use in mounting contact lenses in the eyes of a user of contact lenses, especially soft lenses.

1 Claim, 4 Drawing Figures

U.S. Patent  May 9, 1978  4,088,359

CONTACT LENS INSERTER

SUMMARY OF THE INVENTION

Contact lenses are quite small and are very subject to damage by abrasion if they fall on the ground or even on a carpeted floor where they may also pick up dust particles which must be disposed of before the lens may be mounted on the user's eye.

It is an object of the present invention to provide an instrument for use of contact lens wearers that reduces the hazard of dropping the lens, and facilitates the operation of mounting the lens.

DESCRIPTION OF THE PREFERRED EMBODIMENT

Figure 1:
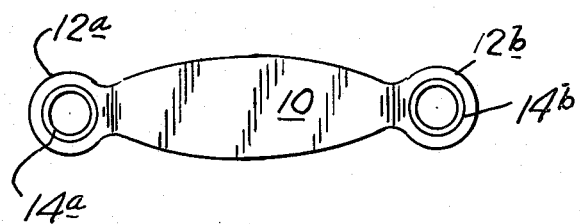
FIG. 1 is a plan view of the instrument.
Figure 2:
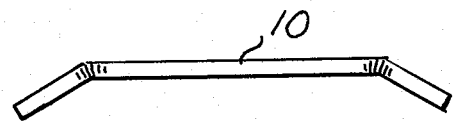
FIG. 2 is an elevation of the instrument.
Figure 3:
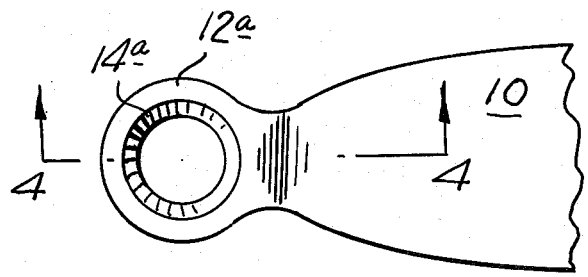
FIG. 3 is an enlarged detailed view of one end of the instrument.
Figure 4:
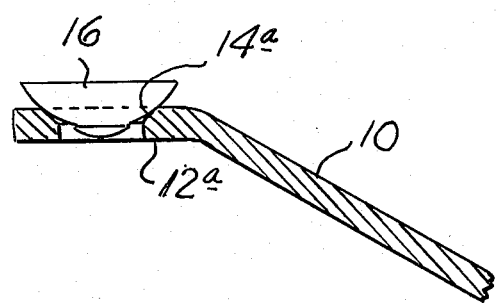
FIG. 4 is a section taken on line 4—4 of FIG. 3 showing a lens in position on the instrument.

Users of contact lenses, in order to mount the lens on an eye, will balance the lens on a fingertip, then, bending forward will bring the lens up to the eye. If there is a tremor of the hand, any slight turn of the insertion finger one way or another it will result in the soft contact lens rolling off the finger, this is due to the extreme convex curve of the soft contact lens resting on the relatively flat surface of the insertion finger. Another danger is an eyelid blink reflex which could cause the contact lens to fall. Still another danger is the possibility of corneal abrasions due to fingernails when not using an inserter and also the transferring of substances such as nicotine, skin care moisturizers, mascara, grease and other foreign substances carried directly from the finger to the eye. These are the hazards which are avoided through the use of such an inserter. The Federal Drug Administration has strict procedures for soft lens storage which include thermal and/or chemical disinfection of the soft lenses daily. The removal from the case to insert the soft lens with one's own hand lessens the cleanliness of such extensive measures, also avoiding the possibility of leaving finger prints on the lenses which will cause lessening of the efficiency of the lens.

The instrument comprises a handle portion 10 at each end of which is a lens holder 12a or 12b set at an angle to handle 10, the angle between lens holder 12a and handle portion 10 being different from the angle between lens holder 12b and the handle portion 10. This difference in angle, through not extreme, is desirable. In order to avoid contact of the hand with the nose when applying a lens, for right handed persons, to the left eye, the greater angle maybe required.

Each lens holder 12a or 12b is a loop of non-abrasive, relatively soft material having an interior beveled surface 14a or 14b which maybe generally conical so as to present a surface tangential to the surface of a lens 16 mounted thereon.

It will be noted that the only contact between the lens and the instrument is along a circle near the edge of the lens and is of a diameter to provide a stable support for the lens so that it may be used by persons with a tremor to apply his contact lenses.

The instrument as shown is of fairly rigid plastic material and of a single piece. The device may be made of other materials and may have a handle portion 10 of a different material than the loop portions 12a and 12b.

The center opening in both ends of the inserter have been left open for visual application by using the opening as a point of fixation for the eye to see through. The opening, besides having the use of a fixation point, also carries the soft contact lens, which in turn contains the necessary visual correction for proper vision during the contact lens insertion procedure.

The instrument may be used for both soft and hard type contact lenses.

Having thus described the preferred embodiment of the invention it should be understood that numerous structural modifications and adaptations may be resorted to without departing from the spirit of the invention.

What is claimed is:

1. An instrument for mounting soft contact lenses on the eye of a contact lens user comprising a handle portion having two opposed flat surfaces and a bulbous central portion and tapered neck portions at the opposed extremities of said handle portion, loop elements disposed at the extremities of said handle portion connected to said tapered neck portions, further including beveled surfaces on an inner portion of each loop element to provide a nesting surface for the soft contact lenses on said loop elements, and said loop elements are each offset relative to said flat handle portion surfaces at different angles but both less than 90° to provide a different angle of attack for lens insertion, and in which the bulbous central portion has a width somewhat greater than a diameter of said loop elements and said tapered neck portions have a width somewhat less than the diameter of said loop elements so as to provide a grasping area which can accommodate a portion of the user's hand.

* * * * *